United States Patent
Fack et al.

(10) Patent No.: US 10,071,040 B2
(45) Date of Patent: Sep. 11, 2018

(54) COSMETIC COMPOSITION COMPRISING A CATION, A LIQUID FATTY SUBSTANCE AND A SORBITAN ESTER, AND COSMETIC TREATMENT PROCESS

(75) Inventors: Géraldine Fack, Levallois (FR); Véronique Mahe, Vaux S/Seine (FR)

(73) Assignee: L'Oreal, Paris (FR)

( * ) Notice: Subject to any disclaimer, the term of this patent is extended or adjusted under 35 U.S.C. 154(b) by 797 days.

(21) Appl. No.: 11/589,214

(22) Filed: Oct. 30, 2006

(65) Prior Publication Data

US 2007/0104671 A1    May 10, 2007

Related U.S. Application Data

(60) Provisional application No. 60/736,296, filed on Nov. 15, 2005.

(30) Foreign Application Priority Data

Oct. 28, 2005   (FR) ..................... 05 53284

(51) Int. Cl.
| | | |
|---|---|---|
| *A61K 8/41* | (2006.01) | |
| *A61K 8/37* | (2006.01) | |
| *A61K 8/49* | (2006.01) | |
| *A61K 8/31* | (2006.01) | |
| *A61K 8/34* | (2006.01) | |
| *A61K 8/92* | (2006.01) | |
| *A61Q 5/12* | (2006.01) | |

(52) U.S. Cl.
CPC .............. *A61K 8/4973* (2013.01); *A61K 8/31* (2013.01); *A61K 8/342* (2013.01); *A61K 8/37* (2013.01); *A61K 8/416* (2013.01); *A61K 8/4946* (2013.01); *A61K 8/922* (2013.01); *A61Q 5/12* (2013.01)

(58) Field of Classification Search
None
See application file for complete search history.

(56) References Cited

U.S. PATENT DOCUMENTS

| | | |
|---|---|---|
| 4,137,180 A | 1/1979 | Naik et al. |
| 4,217,914 A | 8/1980 | Jacquet et al. |
| 4,240,450 A | 12/1980 | Grollier et al. |
| 4,422,853 A | 12/1983 | Jacquet et al. |
| 4,445,521 A | 5/1984 | Grollier et al. |
| 4,839,166 A | 6/1989 | Grollier et al. |
| 4,874,554 A | 10/1989 | Lange et al. |
| 4,948,579 A | 8/1990 | Jacquet et al. |
| 4,957,732 A | 9/1990 | Grollier et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,196,189 A | 3/1993 | Jacquet et al. |
| 5,814,341 A * | 9/1998 | Fankhauser et al. ......... 424/493 |
| 5,958,392 A | 9/1999 | Grollier et al. |
| 6,117,436 A * | 9/2000 | Flemming et al. ........... 424/401 |
| 2001/0009909 A1 | 7/2001 | Maubru et al. |
| 2001/0033270 A1 | 10/2001 | Osawa et al. |
| 2004/0151746 A1 * | 8/2004 | Dubief et al. ................. 424/401 |
| 2004/0197287 A1 | 10/2004 | Kaczvinsky, Jr. et al. |
| 2004/0223938 A1 * | 11/2004 | Li et al. .................... 424/70.13 |
| 2004/0247551 A1 | 12/2004 | Yokomaku et al. |

FOREIGN PATENT DOCUMENTS

| | | |
|---|---|---|
| EP | 0 186 507 A2 | 7/1986 |
| EP | 0 337 354 B1 | 10/1989 |
| EP | 0 342 834 B1 | 11/1989 |
| EP | 1369104 A1 | 12/2003 |
| FR | 2 589 476 A1 | 5/1987 |
| JP | 11-286415 A | 10/1989 |
| JP | 03-287509 A | 12/1991 |
| JP | 04-112812 A | 4/1992 |
| JP | 9-165320 A | 6/1997 |
| JP | 10-152421 A | 6/1998 |
| JP | 2001-206823 A | 7/2001 |
| JP | 2001-226217 A | 8/2001 |
| JP | 2002-265335 A | 9/2002 |
| JP | 2002-348217 A | 12/2002 |
| JP | 2004-010615 A | 1/2004 |
| JP | 2004-091333 A | 3/2004 |
| JP | 2004-238356 A | 8/2004 |
| WO | 99/39684 A1 | 8/1999 |

(Continued)

OTHER PUBLICATIONS

French Search Report for FR 0553284, dated Jul. 11, 2006.
M.R. Porter, BSc, PhD, CChem, MRSC, "Handbook of Surfactants," Blackie & Son Ltd., Glasgow & London, pp. 116-178 (1991).
Charles Todd et al., "Volatile silicone fluids for cosmetic formulations," Cosmetics and Toiletries, vol. 91, pp. 29-32 (1976).
English language abstract of FR 2 589 476 A1, May 7, 1987.
French Search Report for FR 0553285, dated Jul. 11, 2006.
Dorgan, Patrick D., "Waxes in Cosmetics," Drug and Cosmetic Industry, vol. 133, No. 6, (1983), pp. 30-33.

(Continued)

*Primary Examiner* — Mina Haghighatian
*Assistant Examiner* — Luke E Karpinski
(74) *Attorney, Agent, or Firm* — The Marbury Law Group, PLLC

(57) ABSTRACT

The present disclosure relates to a cosmetic composition comprising, in a cosmetically acceptable aqueous medium, at least one cationic surfactant, at least one oxyethylenated ester of sorbitan and at least one non-silicone liquid fatty substance, the liquid fatty substance being present in an amount of less than 8% by weight relative to the total weight of the composition. Another aspect of the present disclosure relates to a cosmetic process for treating keratin materials, such as the hair.

The compositions as disclosed herein have an improved conditioning effect, for instance by smoothing the tips of the hair and providing improved hair sheen.

22 Claims, No Drawings

(56) References Cited

FOREIGN PATENT DOCUMENTS

WO    2004/093835 A1    11/2004
WO    2005/030153 A1    4/2005
WO    2005/077323 A1    8/2005

OTHER PUBLICATIONS

English translation of Japanese Office Action for JP 2006-293141, dated Jan. 31, 2011.
Non-Final Office Action for copending U.S. Appl. No. 11/589,215, dated Jul. 30, 2010 (now abandoned).
Final Office Action for copending U.S. Appl. No. 11/589,215, dated Jan. 5, 2011 (now abandoned).
Non-Final Office Action for copending U.S. Appl. No. 11/589,215, dated Oct. 3, 2011 (now abandoned).
Non-Final Office Action for copending U.S. Appl. No. 11/589,215, dated Jul. 1, 2013 (now abandoned).
Final Office Action for copending U.S. Appl. No. 11/589,215, dated Jan. 1, 2016 (now abandoned).
Non-Final Office Action for copending U.S. Appl. No. 11/589,215, dated Mar. 26, 2015 (now abandoned).
Final Office Action for copending U.S. Appl. No. 11/589,215, dated Oct. 27, 2015 (now abandoned).
Non-Final Office Action for copending U.S. Appl. No. 15/138,606, dated Jun. 1, 2017.

* cited by examiner

COSMETIC COMPOSITION COMPRISING A CATION, A LIQUID FATTY SUBSTANCE AND A SORBITAN ESTER, AND COSMETIC TREATMENT PROCESS

This application claims benefit of U.S. Provisional Application No. 60/736,296, filed Nov. 15, 2005, the contents of which are incorporated herein by reference. This application also claims benefit of priority under 35 U.S.C. § 119 to French Patent Application No. FR 05 53284, filed Oct. 28, 2005, the contents of which are also incorporated herein by reference.

The present disclosure relates to a cosmetic composition, for example a hair conditioner, comprising at least one cationic surfactant, at least one oxyethylenated sorbitan ester and at least one liquid fatty substance in a particular ratio, and to a cosmetic process for treating keratin materials, such as the hair.

It is well known that hair that has been sensitized (i.e., damaged and/or embrittled) to varying degrees under the action of atmospheric agents or under the action of mechanical or chemical treatments, such as dyeing, bleaching and/or permanent-waving, is often difficult to disentangle and to style, and may lack softness.

Cosmetic compositions comprising cationic surfactants have already been proposed for treating keratin materials, such as the hair.

However, such compositions may have drawbacks such as rinseability problems, stability problems, difficulties in distributing them over the keratin materials and/or also insufficient cosmetic properties.

It has also been recommended to use cationic polymers, cationic silicones or cationic surfactants in compositions for washing or caring for keratin materials such as the hair, to facilitate the disentangling of the hair and/or to give it softness and suppleness. The use of cationic polymers or cations for this purpose may have various drawbacks. On account of their high affinity for the hair, some of these polymers may become deposited in a substantial amount during repeated use, and may lead to undesirable effects such as an unpleasant, laden feel, stiffening of the hair, and/or adhesion between the fibers that affects styling.

Furthermore, the care used for very sensitized hair may still be insufficient to treat the ends, which are usually very damaged.

In summary, it is found that the current conditioning cosmetic compositions are not always entirely satisfactory. Thus, it is sought to obtain cosmetic compositions that have very good cosmetic properties, for instance on very sensitized hair.

The present inventors have now discovered that the combination of at least one cationic surfactant, of at least one oxyethylenated ester of sorbitan and of at least one liquid fatty substance in a particular ratio may allow at least one of these drawbacks to be overcome.

Hair treated with the composition as disclosed herein, may be smooth, may disentangle easily, may be shiny, supple and individualized, and/or may have a soft feel with no feeling of residues. The treated hair may have a natural, unladen appearance. The smoothness may be uniform from the roots to the ends. The ends may show less splitting.

Furthermore, these effects are remanent over time.

The present inventors have discovered that the addition of a weakly oxyethylenated sorbitan ester furthermore makes it possible, surprisingly, to reduce the discomfort reactions (itching, redness, etc.), for example on the scalp, of compositions containing surfactants liable to cause reactions of this type when they are used alone.

Thus, according to the present disclosure, novel cosmetic compositions are now proposed, comprising, in a cosmetically acceptable aqueous medium, at least one cationic surfactant, at least one oxyethylenated ester of sorbitan and of a saturated, linear or branched $C_8$-$C_{30}$ fatty acid with a number of moles of ethylene oxide of less than or equal to 10, and at least one non-silicone fatty substance, and at least one non-silicone fatty substance that is liquid at a temperature of 25° C. and at atmospheric pressure (1 atm), wherein the at least one liquid non-silicone fatty substance is present in an amount of less than or equal to 8% by weight relative to the total weight of the composition.

Another aspect of the present disclosure is a cosmetic process for treating keratin materials, such as the hair, using the above-mentioned composition.

Another aspect of the present disclosure is the use of the composition as a hair conditioner.

Other subjects, characteristics, aspects and advantages of the present disclosure will emerge even more clearly on reading the description and the various examples that follow.

According to the present disclosure, the term "sensitized hair" is generally understood to mean hair that has undergone external physical attack (by light, heat, waves, etc.), mechanical attack (by repeated blow-drying, combing or brushing, etc.) and/or chemical attack (by oxidation dyeing, bleaching, permanent-waving, relaxing, etc.). In at least one embodiment, the compositions according to the present disclosure are effective on hair sensitized by chemical attack.

The term "at least one" will be understood as meaning "one or more", i.e. one, two, three or more.

For purposes of the present disclosure, the term "cosmetically acceptable medium" means a medium that is compatible with any keratin material, such as the skin, the hair, the nails, the eyelashes, the eyebrows or the lips and any other area of the body and of the face.

The saturated fatty acids of the ester of sorbitans of a saturated $C_8$-$C_{30}$ fatty acid, with a number of moles of ethylene oxide of less than or equal to 10, may in at least one embodiment comprise from 8 to 24 carbon atoms, for example, from 8 to 18 carbon atoms. In at least one embodiment, the fatty acids may be chosen from lauric acid and stearic acid. In a further embodiment, the fatty acid is lauric acid.

Monoesters of a $C_8$-$C_{24}$ fatty acid and of oxyethylenated sorbitan may be used in at least one embodiment. For instance the average number of moles of ethylene oxide may range from 3 to 8 mol of ethylene oxide, and in a further embodiment may be equal to 4 mol.

As disclosed herein, the oxyethylenated and saturated, linear or branched $C_8$-$C_{30}$ fatty acid esters of sorbitan having a number of moles of ethylene oxide of less than or equal to 10 generally have the following formula:

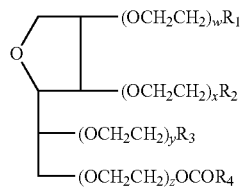

in which w, x and y are numbers ranging from 0 to 9, and equal to 0 in at least one embodiment, z is a number ranging from 1 to 10, for instance ranging from 3 to 8, and in a further embodiment equal to 4, the sum of w+x+y+z is an average value of less than or equal to 10, for instance ranging from 3 to 8, and in a further embodiment equal to 4.

$R_1$, $R_2$ and $R_3$, which may be identical or different, are chosen from H and C(=O)$R_5$ and in at least one embodiment are all H.

$R_4$ is a $C_8$-$C_{30}$ saturated, linear or branched alkyl radical, chosen, for example, from $C_8$-$C_{18}$ $R_5$ is a $C_8$-$C_{30}$ saturated alkyl radicals, chosen, for example, from $C_8$-$C_{18}$.

As disclosed herein, the sorbitan esters include but are not limited to sorbitan monolaurate oxyethylenated with 4 mol of ethylene oxide (4 EO) or polysorbate 21, sorbitan monostearate oxyethylenated with 4 mol of ethylene oxide (4 EO) or polysorbate 61.

According to at least one embodiment of the present disclosure, polysorbate 21 may be used, and is sold under the name TWEEN 21 by the company Uniqema.

According to the present disclosure, the oxyethylenated sorbitan ester may be present in the cosmetic composition in an amount ranging from 0.1% to 10%, for example ranging from 0.5% to 8% or from 1 to 6%, by weight relative to the total weight of the composition.

The composition according to the present disclosure comprises at least one cationic surfactant that is well known per se, such as optionally polyoxyalkylenated primary, secondary or tertiary fatty amine salts and quaternary ammonium salts, and mixtures thereof.

According to the present disclosure, the cationic surfactants are non-polymeric, i.e. they do not comprise any repeating monomer units.

Fatty amines that may be mentioned include, but are not limited to, alkylamidoamines, for instance ($C_8$-$C_{30}$)alkylamidodi($C_1$-$C_6$)alkylamines such as stearamidopropyldimethylamine (MACKINE 301 sold by MacIntyre).

Examples of quaternary ammonium salts that may be mentioned include, but are not limited to:

those having formula (V) below:

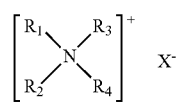

in which $R_1$ to $R_4$, which may be identical or different, are chosen from linear or branched aliphatic radicals containing from 1 to 30 carbon atoms and from aromatic radicals such as aryl or alkylaryl. The aliphatic radicals may comprise heteroatoms such as, for example, oxygen, nitrogen, sulfur and halogens. The aliphatic radicals may be chosen, for example, from
($C_1$-$C_{30}$)alkyl, alkoxy, ($C_2$-$C_6$) polyoxyalkylene, alkylamide, ($C_{12}$-$C_{22}$)alkylamido($C_2$-$C_6$)alkyl, ($C_{12}$-$C_{22}$)alkyl acetate and hydroxyalkyl radicals, containing from 1 to 30 carbon atoms; and X$^-$ is an anion chosen from halides, phosphates, acetates, lactates, ($C_2$-$C_6$)alkyl sulfates and alkylsulfonates or alkylarylsulfonates;

quaternary ammonium salts of imidazoline, for instance those of formula (VI) below:

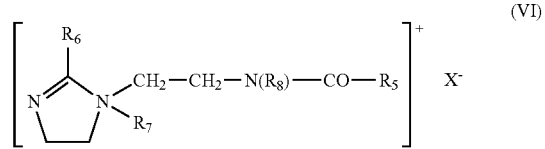

in which $R_5$ is an alkenyl or alkyl radical containing from 8 to 30 carbon atoms, for example fatty acid derivatives of tallow or of coconut, $R_6$ is chosen from a hydrogen atom, a $C_1$-$C_4$ alkyl radical and an alkenyl or alkyl radical containing from 8 to 30 carbon atoms, $R_7$ is a $C_1$-$C_4$ alkyl radical, $R_8$ is chosen from a hydrogen atom and a $C_1$-$C_4$ alkyl radical, and X$^-$ is an anion chosen from halides, phosphates, acetates, lactates, alkyl sulfates, alkylsulfonates and alkylarylsulfonates.

In at least one embodiment, $R_5$ and $R_6$ denote a mixture of alkenyl or alkyl radicals containing from 12 to 21 carbon atoms, for example fatty acid derivatives of tallow, $R_7$ is methyl and $R_8$ is a hydrogen atom. Such a product is, for example, Quaternium-27 (CTFA 2002), Quaternium-87 (CTFA 2002) or Quaternium-83 (CTFA 2002), which are sold under the name "Varisoft®" W575PG by the company Goldschmidt, diquaternary ammonium salts of formula (VII):

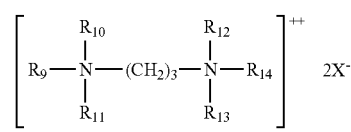

in which $R_9$ is an aliphatic radical containing from 16 to 30 carbon atoms, $R_{10}$, $R_{11}$, $R_{12}$, $R_{13}$ and $R_{14}$, which may be identical or different, are chosen from hydrogen and an alkyl radical containing from 1 to 4 carbon atoms, and X$^-$ is an anion chosen from halides, acetates, phosphates, nitrates, ethyl sulfates and methyl sulfates. Such diquaternary ammonium salts comprise, for instance, propanetallowdiammonium dichloride;

quaternary ammonium salts comprising at least one ester function, such as those of formula (VIII) below:

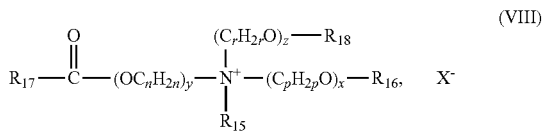

in which:

$R_{15}$ is chosen from $C_1$-$C_6$ alkyl radicals and $C_1$-$C_6$ hydroxyalkyl or dihydroxyalkyl radicals;

$R_{16}$ is chosen from:
a radical

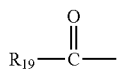

linear or branched, saturated or unsaturated $C_1$-$C_{22}$ hydrocarbon-based radicals $R_{20}$,
a hydrogen atom,
$R_{17}$ is chosen from:
a radical

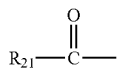

linear or branched, saturated or unsaturated $C_1$-$C_6$ hydrocarbon-based radicals $R_{22}$,
a hydrogen atom,
$R_{17}$, $R_{19}$ and $R_{21}$, which may be identical or different, are chosen from linear or branched, saturated or unsaturated $C_7$-$C_{21}$ hydrocarbon-based radicals;
r, n and p, which may be identical or different, are integers ranging from 2 to 6;
y is an integer ranging from 1 to 10;
x and z, which may be identical or different, are integers ranging from 0 to 10; and
$X^-$ is a simple or complex, organic or inorganic anion;
with the proviso that the sum x+y+z is from 1 to 15, that when x is 0, then $R_{16}$ is $R_{20}$ and that when z is 0, then $R_{18}$ is $R_{22}$.

The alkyl radicals $R_{15}$ may be linear or branched, and in at least one embodiment the alkyl radicals are linear.

In at least one embodiment, $R_{15}$ is chosen from methyl, ethyl, hydroxyethyl and dihydroxypropyl radicals, and in a further embodiment, $R_{15}$ is chosen from methyl and ethyl radicals.

According to at least one embodiment, the sum x+y+z is from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it may contain 1 to 3 carbon atoms.

According to at least one embodiment, $R_{17}$, $R_{19}$ and $R_{21}$, which may be identical or different, are chosen from linear or branched, saturated or unsaturated $C_{11}$-$C_{21}$ hydrocarbon-based radicals, and in a further embodiment from linear or branched, saturated or unsaturated $C_{11}$-$C_{21}$ alkyl and alkenyl radicals.

According to at least one embodiment, x and z, which may be identical or different, are 0 or 1.

According to at least one embodiment, y is equal to 1.

According to at least one embodiment, r, n and p, which may be identical or different, are equal to 2 or 3 and in a further embodiment equal to 2.

The anion $X^-$ may be a halide (chloride, bromide or iodide) or a $C_1$-$C_4$ alkyl sulfate, such as methyl sulfate. However, methanesulfonate, phosphate, nitrate, tosylate, an anion derived from an organic acid, such as acetate or lactate, or any other anion that is compatible with the ammonium containing an ester function may also be used.

For example, in one embodiment, the anion $X^-$ may be chosen from chloride and methyl sulfate.

According to at least one embodiment of the present disclosure, use may be made in the presently disclosed composition of the ammonium salts of formula (IV) in which:
$R_{15}$ is a methyl or ethyl radical,
x and y are equal to 1;
z is equal to 0 or 1;
r, n and p are equal to 2;
$R_{16}$ is chosen from:
a radical

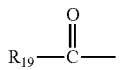

methyl, ethyl or $C_{14}$-$C_{22}$ hydrocarbon-based radicals,
a hydrogen atom;
$R_{18}$ is chosen from:
a radical

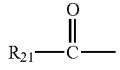

a hydrogen atom;
$R_{17}$, $R_{19}$ and $R_{21}$, which may be identical or different, are chosen from linear or branched, saturated or unsaturated $C_{13}$-$C_{17}$ hydrocarbon-based radicals, and in at least one embodiment are chosen from linear or branched, saturated or unsaturated $C_{13}$-$C_{17}$ alkyl and alkenyl radicals.

According to at least one embodiment of the present disclosure, the hydrocarbon-based radicals are linear.

Non-limiting examples of compounds of formula (VIII) that may be mentioned include the salts (such as chloride or methyl sulfate) of diacyloxyethyidimethylammonium, of diacyloxyethylhydroxyethylmethylammonium, of monoacyloxyethyldihydroxyethylmethylammonium, of triacyloxyethylmethylammonium, of monoacyloxyethylhydroxyethyldimethylammonium, and mixtures thereof. The acyl radicals may contain 14 to 18 carbon atoms and may be derived from a plant oil, for instance palm oil or sunflower oil. When the compound contains several acyl radicals, these radicals may be identical or different.

These products are obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification is followed by a quaternization using an alkylating agent such as an alkyl halide (such as a methyl or ethyl halide), a dialkyl sulfate (such as dimethyl or diethyl sulfate), methyl methanesulfonate, methyl para-toluenesulfonate, glycol chlorohydriri or glycerol chlorohydrin.

Such compounds are sold, for example, under the names Dehyquart® by the company Cognis, Stepanquat® by the company Stepan, Noxamium® by the company Ceca, and Rewoquat® WE 18 by the company Rewo-Goldschmidt.

The composition according to the present disclosure may, in at least one embodiment, comprise a mixture of quaternary ammonium mono-, di- and triester salts with a weight majority of diester salts.

Examples of mixtures of ammonium salts that may be used include the mixture comprising 15% to 30% by weight of acyloxyethyldihydroxyethylmethylammonium methyl sulfate, from 45% to 60% of diacyloxyethylhydroxylethylmethylammonium methyl sulfate and from 15% to 30% of triacyloxyethylmethylammonium methyl sulfate, the acyl radicals containing from 14 to 18 carbon atoms and being derived from optionally partially hydrogenated palm oil.

It is also possible to use the ammonium salts comprising at least one ester function described in U.S. Pat. Nos. 4,874,554 and 4,137,180.

Among the quaternary ammonium salts mentioned above that may used, for example, are those corresponding to formula (V). Non-limiting mention may be made firstly of tetraalkylammonium chlorides, for instance dialkyldimethylammonium or alkyltrimethylammonium chlorides in which the alkyl radical contains from about 12 to 22 carbon atoms, such as behenyltrimethylammonium, distearyldimethylammonium, cetyltrimethylammonium or benzyldimethylstearylammonium chlorides, or alternatively, secondly, palmitylamidopropyltrimethylammonium chloride or stearamidopropyldimethyl-(myristyl acetate)ammonium chloride corresponding to Quaternium-70 (CTFA 2002) sold under the name Ceraphyl® 70 by the company ISP.

The cationic surfactants that may be used in the composition of the present disclosure can be chosen from quaternary ammonium salts, such as from behenyltrimethylammonium chloride, cetyltrimethylammonium chloride, Quaternium-83, Quaternium-87, behenylamidopropyl-2,3-dihydroxypropyldimethylammonium chloride, palmitylamidopropyltrimethylammonium chloride and stearamidopropyldimethylamine.

The composition according to the present disclosure comprises the at least one cationic surfactant in an amount ranging from 0.01% to 10% by weight, for instance ranging from 0.05% to 4% by weight relative to the total weight of the composition and further, in at least one embodiment, from 0.1 to 3% by weight.

According to the present disclosure, the term "non-silicone fatty substance" means any oily organic substance not comprising any silicone atoms in its elemental structure, comprising at least one carbon-based chain containing at least 10 carbon atoms, and whose solubility in water at 25° C. (1 atm) is less than 0.1% by weight.

The non-silicone liquid fatty substances may be chosen from oxyethylenated or non-oxyethylenated fatty alcohols, fatty esters, plant oils and hydrocarbon-based oils, and mixtures thereof.

The fatty alcohols according to the present disclosure may be branched and/or unsaturated, and contain from 12 to 40 carbon atoms.

According to at least one embodiment, the fatty alcohols have the structure R—OH, in which R is chosen from a $C_{12}$-$C_{24}$ branched alkyl or $C_{12}$-$C_{24}$ alkenyl group. R may also be substituted with at least one hydroxyl group but, according to at least one embodiment, R does not contain any hydroxyl groups.

Examples that may be mentioned include, but are not limited to, oleyl alcohol, isocetyl alcohol, isostearyl alcohol, octyldodecanol and 2-ethylhexyldodecanol, and mixtures thereof.

The fatty alcohol may represent a mixture of fatty alcohols, which means that several fatty alcohol species may coexist, in the form of a mixture, in a commercial product.

According to the present disclosure, the term "oxyalkylenated fatty alcohol" means any fatty alcohol having the following structure:

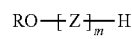

in which:
R is a linear or branched, saturated or unsaturated radical containing from 8 to 40, for example, from 8 to 30, carbon atoms,
Z is chosen from an oxyethylenated (i) and/or oxypropylenated (ii)1 and (ii)2 radical having the following respective formulae:

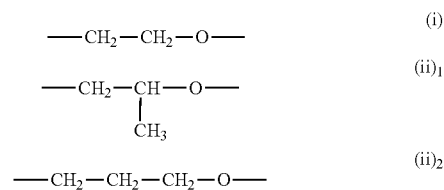

m is the number of ethylene oxide (i) and/or propylene oxide (ii)1 or (ii)2 groups, ranging from 1 to 20 and according to at least one embodiment from 2 to 10.

Liquid oxyalkylenated fatty alcohols that may be used, according to the present disclosure, are linear, saturated or unsaturated fatty alcohols containing from 10 to 20 carbon atoms and 2 to 8 ethylene oxide groups.

According to at least one embodiment, the compounds of oxyalkylenated fatty alcohol type that may be used include the following commercial products:
MERGITAL LM2 (Cognis) [lauryl alcohol 2 EO];
EMPILAN KA 2.5/90FL (Albright & Wilson) and MERGITAL BL309 (Cognis) [decyl alcohol 3 EO];
EMPILAN KA 5/90FL (Albright & Wilson) and MERGITAL BL589 (Cognis) [decyl alcohol 5 EO];
EMULGIN 05 (Cognis) [oleocetyl alcohol 5 EO];
WITCONOL APM (Goldschmidt) [myristyl alcohol 3 PO].

According to at least one embodiment, the fatty alcohols of the present disclosure are non-oxyalkylenated. These fatty alcohols may be constituents of animal or plant waxes.

In at least one embodiment, the liquid fatty esters are liquid carboxylic acid esters that may be used contain at least 10 carbon atoms and, according to at least one further embodiment, from 10 to 40 carbon atoms, for instance purcellin oil (stearyl octanoate), isopropyl myristate, isopropyl palmitate, butyl stearate, hexyl laurate, diisopropyl adipate, isononyl isononanoate, 2-ethylhexyl palmitate, 2-octyldodecyl lactate, isostearyl neopentanoate, tridecyl neopentanoate, isocetyl neopentanoate and isoarachidyl neopentanoate, and mixtures thereof.

The plant oils may be chosen from sweet almond oil, avocado oil, castor oil, olive oil, jojoba oil, sunflower oil, wheat germ oil, sesame seed oil, groundnut oil, grapeseed oil, soybean oil, rapeseed oil, safflower oil, coconut oil, corn oil, hazelnut oil, shea butter, palm oil, apricot kernel oil, cade oil, liquid jojoba wax and beauty-leaf oil, and mixtures thereof.

Hydrocarbon-based oils that may be mentioned include but are not limited to mineral oils, such as liquid paraffin and liquid petroleum jelly, and isoparaffins such as polyisobutylenes and polydecenes; and mixtures thereof.

The liquid fatty substance(s) may be present in the composition in an amount ranging from 0.05% to 8%, for instance from 0.1% to 5% and further, for example, from 0.5% to 3% by weight relative to the total weight of the composition.

The composition according to the present disclosure may optionally contain surfactants other than the above-described at least one cationic surfactant.

The additional surfactants may be present in an amount ranging from about 0.1% to 10%, such as from 0.5% to 8% and even further, for example, from 1% to 5% by weight relative to the total weight of the composition.

In at least one embodiment, the additional surfactants are chosen from nonionic surfactants.

Nonionic surfactants are compounds that are well known per se (see "Handbook of Surfactants" by M. R. Porter, published by Blackie & Son (Glasgow and London), 1991, pp. 116-178) and, as disclosed herein, the nature of the nonionic surfactant is not a critical feature. Thus, they can be chosen from (non-limiting list) polyethoxylated, polypropoxylated or polyglycerolated fatty alcohols, polyethoxylated, polypropoxylated or polyglycerolated α-diols, polyethoxylated, polypropoxylated or polyglycerolated alkylphenols, and polyethoxylated, polypropoxylated or polyglycerolated fatty acids, all these compounds having a fatty chain containing, for example, 8 to 18 carbon atoms, it being possible for the number of ethylene oxide or propylene oxide groups to range from 2 to 50 and for the number of glycerol groups to range for instance from 2 to 30. Non-limiting mention may also be made of copolymers of ethylene oxide and of propylene oxide, condensates of ethylene oxide and of propylene oxide with fatty alcohols; polyethoxylated fatty amides having, in at least one embodiment, from 2 to 30 mol of ethylene oxide, polyglycerolated fatty amides containing on average 1 to 5, such as 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)-alkylamine oxides or N-acylaminopropylmorpholine oxides.

The compositions according to the present disclosure include non-washing (non-detergent) compositions, and may, in at least one embodiment, comprise less than 4% by weight of detergent surfactants, such as anionic surfactants, relative to the total weight of the composition and further, for example, less than 1% by weight of detergent surfactants, such as anionic surfactants relative to the total weight of the composition. Further, in still another embodiment, the composition as disclosed herein does not contain any detergent surfactants.

The composition according to the present disclosure may also comprise at least one additional conditioning agent. This conditioning agent may be chosen from silicones, cationic polymers, solid carboxylic fatty esters and mixtures thereof.

As disclosed herein, the silicones that may be used may be soluble or insoluble in the composition, and, in at least one embodiment, they may be polyorganosiloxanes that are insoluble in the composition of the present disclosure. They may be in the form of oils, waxes, resins or gums. They may also be used pure or as an emulsion, a dispersion or a microemulsion.

The organopolysiloxanes are defined in greater detail in Walter Noll's "Chemistry and Technology of Silicones" (1968) Academic Press. They can be volatile or non-volatile.

When they are volatile, the silicones may be chosen from those having a boiling point ranging from 60° C. to 260° C., and even further from:

(i) cyclic silicones containing from 3 to 7, for example from 4 to 5 silicone atoms. These are, for example, octamethylcyclotetrasiloxane sold under the name "Volatile Silicone 7207" by Union Carbide or "Silbione 70045 V 2" by Rhodia, decamethylcyclopentasiloxane sold under the name "Volatile Silicone 7158" by Union Carbide, and "Silbione 70045 V 5" by Rhodia, and mixtures thereof.

Non-limiting mention may also be made of cyclocopolymers of the dimethylsiloxane/methylalkylsiloxane type, such as "Silicone Volatile FZ 3109" sold by the company Union Carbide, having the chemical structure:

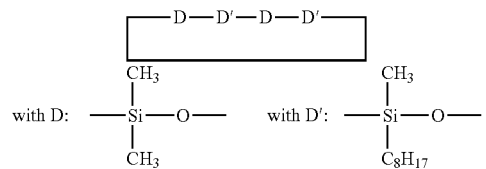

Non-limiting mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms, and having a viscosity of less than or equal to $5 \times 10^{-6}$ m²/s at 25° C. An example is decamethyltetrasiloxane sold under the name "SH 200" by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

As disclosed herein, the non-volatile silicones that may be mentioned include but are not limited to: polyalkylsiloxanes, polyarylsiloxanes, polyalkylarylsiloxanes, silicone gums and resins, polyorganosiloxanes modified with organofunctional groups, and also mixtures thereof.

The organomodified silicones that can be used in accordance with the present disclosure are silicones as defined above and containing in their structure at least one organofunctional groups attached via a hydrocarbon-based group.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for instance, $C_1$-$C_4$ aminoalkyl groups;

thiol groups, such as the products sold under the names "GP 72 A" and "GP 71" from Genesee;

alkoxylated groups, such as the product sold under the name "Silicone Copolymer F-755" by SWS Silicones and Abil Wax® 2428, 2434 and 2440 by the company Goldschmidt;

hydroxylated groups, such as the polyorganosiloxanes containing a hydroxyalkyl function, described in French Patent Application No. FR-A-85/16334, now published as FR 2 589 476;

acyloxyalkyl groups, such as, for example, the polyorganosiloxanes described in U.S. Pat. No. 4,957,732;

anionic groups of the carboxylic acid type, such as, for example, in the products described in European Patent No. EP 186 507 from the company Chisso Corporation, or of the alkylcarboxylic type, such as those present in the product X-22-3701$^E$ from the company Shin-Etsu; 2-hydroxyalkyl sulfonate; 2-hydroxyalkyl thiosulfate such as the products sold by the company Goldschmidt under the names "Abil® S201" and "Abile® S255";

hydroxyacylamino groups, such as the polyorganosiloxanes described in European Patent Application No. EP 342 834. Non-limiting mention may be made, for example, of the product Q2-8413 from the company Dow Corning.

Examples of silicones that may be used include polydimethylsiloxanes, polyalkylarylsiloxanes and polydimethylsiloxanes containing amino or alkoxylated groups.

The cationic polymers that may be used in accordance with the present disclosure may be chosen from any of those already known per se as improving the cosmetic properties of hair treated with detergent compositions, i.e. those described in European Patent Application No. EP-A-0 337 354 and in French Patent Application Nos. FR-A-2 270 846, 2 383 660, 2 598 611, 2 470 596 and 2 519 863.

Even more generally, for the purposes of the present disclosure, the expression "cationic polymer" denotes any polymer containing cationic groups and/or groups that may be ionized into cationic groups.

Among all the cationic polymers that may be used in the context of the present disclosure, at least one embodiment uses quaternary cellulose ether derivatives such as the products sold under the name "JR 400" by the company Amerchol, cyclopolymers, for instance homopolymers of diallyldimethylammonium salt and copolymers of diallyidimethylammonium salt and of acrylamide, for example the chlorides sold under the names "Merquat 100", "Merquat 550" and "Merquat S" by the company Nalco, cationic polysaccharides, such as guar gums modified with 2,3-epoxypropyltrimethylammonium chloride, sold, for example, under the name "Jaguar C13S" by the company Meyhall, optionally crosslinked homopolymers and copolymers of (meth)acryloyloxyethyltrimethylammonium salt, sold by the company Ciba as a 50% solution in mineral oil under the trade names Salcare® SC92 (crosslinked copolymer of methacryloyloxyethyltrimethylammonium chloride and of acrylamide) and Salcare® SC95 (crosslinked homopolymer of methacryloyloxyethylirimethylammonium chloride).

It is also possible to use polymers comprising repeating units corresponding to the formula:

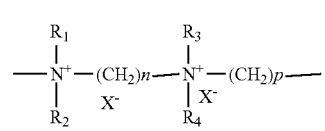

(a)

in which $R_1$, $R_2$, $R_3$ and $R_4$, which may be identical or different, are chosen from alkyl and hydroxyalkyl radicals comprising from 1 to 4 carbon atoms, n and p are integers ranging from 2 to 20, and $X^-$ is an anion derived from a mineral or organic acid.

The additional conditioning agents that may be used in the composition according to the present disclosure may be present in an amount ranging from 0.01% to 20% by weight, for instance ranging from 0.1% to 10% by weight and according to a further embodiment, ranging from 0.3% to 5% by weight relative to the total weight of the composition.

For instance, the cosmetically acceptable medium may be aqueous and may comprise water or a mixture of water and of a cosmetically acceptable solvent such as a $C_1$-$C_4$ lower alcohol, for example ethanol, isopropanol, tert-butanol or n-butanol; polyols, for instance propylene glycol or glycerol; polyol ethers; $C_5$-$C_{10}$ alkanes; and mixtures thereof. According to at least one embodiment, the solvents may be chosen from glycerol and propylene glycol.

The cosmetically acceptable medium, which, in at least one embodiment, is aqueous, is present in an amount ranging from 30% to 98% by weight relative to the total weight of the composition.

The solvents may be present in concentrations ranging from 0.5% to 30% by weight relative to the total weight of the composition.

The pH of the compositions of the invention may range from 2 to 8, and further from 3 to 7.

The compositions according to the present disclosure may also contain standard additives that are well known in the art, such as anionic, nonionic or amphoteric polymers, non-polymeric thickeners, for instance acids or electrolytes, opacifiers, nacreous agents, vitamins, provitamins such as panthenol, fragrances, dyes, organic or mineral particles, preserving agents, pH stabilizers, antidandruff agents, for instance piroctone olamine, hair-loss counteractants.

A person skilled in the art will take care to select the optional additives and the amount thereof such that they do not harm the beneficial properties of the compositions of the present disclosure.

These additives are present in the composition according to the present disclosure in an amount ranging from 0% to 20% by weight relative to the total weight of the composition.

The compositions of the present disclosure may be in the form of a rinse-out or leave-in hair conditioner, compositions for permanent-waving, relaxing, dyeing or bleaching, or alternatively in the form of rinse-out compositions to be applied before or after a dyeing, bleaching, permanent-waving or relaxing operation or alternatively between the two steps of a permanent-waving or hair-relaxing operation.

They may be used, for example, as hair conditioners, care products, deep-down care masks or scalp treatment lotions or creams. These compositions may be rinse-out or leave-in compositions.

According to at least one embodiment of the present disclosure, the composition may be used as a hair conditioner, for instance, a hair conditioner that can be used on sensitized hair. This hair conditioner may be a rinse-out or leave-in hair conditioner, and according to at least one embodiment is a rinse-out hair conditioner.

The cosmetic compositions according to the present disclosure may be in the form of a gel, a milk, a cream, an emulsion, fluid or thickened lotions or a foam, and may be used for the skin, the nails, the eyelashes, the lips, and the hair, for example.

The compositions may be packaged in various forms, for instance, in vaporizers, pump-dispenser bottles or in aerosol containers in order to dispense the composition in vaporized form or in the form of a mousse. Such packaging forms are indicated, for example, when it is desired to obtain a spray, a lacquer or a mousse for treating the hair.

The present disclosure also relates to a cosmetic process for treating keratin materials such as, for example, the skin or the hair, which comprises applying to the keratin materials an effective amount of a cosmetic composition as described above, and optionally rinsing it off after optionally leaving it to act for a period of time.

The rinsing is performed, for example, with water.

Thus, this process according to the present disclosure allows the treatment, conditioning and care of the hair or any other keratin material.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Examples 1 to 5

The following hair-conditioning compositions were prepared:
1. All water was introduced into the manufacturing tank, and then the water-soluble compounds were added, with the exception of the oxyethylenated sorbitan ester(s). The mixture was heated to 80° C. with stirring using a doctor blade, until fully dissolved.
2. The water-insoluble compounds were introduced apart from the fragrances and the silicones into an additional tank. The mixture was heated to 80° C.
3. The contents of the additional tank and the silicones, if any, were introduced into the manufacturing tank and emulsified for 10 minutes with vigorous turbomixer and doctor blade stirring, while the temperature was maintained. Then, the mixture was cooled.
4. At 30° C., the oxyethylenated sorbitan ester and the fragrances were introduced with doctor blade stirring.

| Example 1 of a rinse-out hair conditioner: | |
|---|---|
| | In g AM |
| Oxyethylenated (4 EO) lauryl alcohol (BRIJ 30 from Uniqema) | 1 |
| Palm oil (Refined palm oil from Welch Holme & Clark) | 1 |
| Cetyltrimethylammonium chloride at 25% AM (ARQUAD 16-25 lo from Akzo Nobel) | 0.45 |
| Stearylamidopropyldimethylamine (MACKINE 301 from MacIntyre) | 0.75 |
| Sorbitan monolaurate oxyethylenated with 4 EO (TWEEN 21 from Uniqema) | 4 |
| Polydimethylsiloxane containing aminoethyl iminopropyl end groups (Dow Corning 939 Emulsion) | 0.63 |
| Fragrance | qs |
| Preserving agents | qs |
| Water | qs 100 g |

| Example 2 of leave-in hair conditioner: | |
|---|---|
| | In g AM |
| Polyethylene glycol monoisostearate (PRISORINE 3644 from Uniqema) | 0.25 |
| Behenyltrimethylammonium chloride at 80% AM (GENAMIN KDMP from Clariant) | 0.20 |
| Avocado oil (LIPOVOl A from Lipo Chemicals) | 0.65 |
| Liquid jojoba wax | 0.65 |
| Ethanol | 14.3 |
| 2,4-Diaminopyridine 3-oxide (MEXORYL SAG from Chimex) | 1.5 |
| Cyclopentadimethylsiloxane (MIRASIL CM 5 from Rhodia) | 0.45 |
| Sorbitan monolaurate oxyethylenated with 4 mol of ethylene oxide (4 EO) (TWEEN 21 from Uniqema) | 0.5 |
| Fragrance, preserving agents | qs |
| Water | qs 100 g |

| Example 3 of leave-in antidandruff hair conditioner: | |
|---|---|
| | In g AM |
| Polyethylene glycol monoisostearate (PRISORINE 3644 from Uniqema) | 0.25 |
| Behenyltrimethylammonium chloride at 80% AM (GENAMIN KDMP from Clariant) | 0.2 |
| Avocado oil (LIPOVOL A from Lipo Chemicals) | 0.65 |
| Liquid jojoba wax (Pure jojoba oil from Jojoba Israel) | 0.65 |
| Ethanol | 14.3 |
| Piroctone olamine (OCTOPIROX from Clariant) | 0.1 |
| Cyclopentadimethylsiloxane (MIRASIL CM 5 from Rhodia) | 0.45 |
| Sorbitan monolaurate oxyethylenated with 4 EO (TWEEN 21 from Uniqema) | 0.5 |
| Fragrance, preserving agents | qs |
| Water | qs 100 g |

| Example 4 of rinse-out hair conditioner: | |
|---|---|
| | In g AM |
| Oxyethylenated (4 EO) lauryl alcohol (BRIJ 30 from Uniqema) | 3 |
| Palm oil (Refined palm oil from Welch Holme & Clark) | 1 |
| Pregelatinized hydroxypropylated corn distarch phosphate (Structure Zea from National Starch) | 6 |

-continued

Example 4 of rinse-out hair conditioner:

| | In g AM |
|---|---|
| Cetyltrimethylammonium chloride at 25% AM (ARQUAD 16-25 lo from Akzo Nobel) | 0.45 |
| Stearylamidopropyldimethylamine (MACKINE 301 from MacIntyre) | 0.75 |
| Sorbitan monolaurate oxyethylenated with 4 EO (TWEEN 21 from Uniqema) | 4 |
| Polydimethylsiloxane containing aminoethyl iminopropyl groups at 35% AM (Dow Corning 939 Emulsion) | 0.63 |
| Fragrance | qs |
| Preserving agent | qs |
| Kaolinite (SUPREME from Ymeris) | 3 |
| Water | qs 100 g |

Example 5 of rinse-out or leave-in hair conditioner:

| | In g AM |
|---|---|
| Perhydrosqualene (squalane from Kishimoto) | 1.85 |
| Behenyltrimethylammonium chloride at 80% AM (GENAMIN KDMP from Clariant) | 0.31 |
| Cyclopentadimethylsiloxane (MIRASIL CM 5 from Rhodia) | 2.1 |
| Propylene glycol | 2 |
| Liquid jojoba wax (pure jojoba oil from Jojoba Israel) | 1.05 |
| Sorbitan monolaurate oxyethylenated with 4 mol of ethylene oxide (TWEEN 21 from Uniqema) | 5 |
| Water | qs 100 g |

These compositions were applied to highly sensitized hair. The cosmetic properties (disentangling, smoothing, suppleness and sheen) were excellent and uniform from the roots to the ends of the hair.

Between two applications, the hair remained soft, supple and smooth.

What is claimed is:

1. A cosmetic composition comprising, in a cosmetically acceptable aqueous medium:
   at least one cationic surfactant;
   at least one oxyethylenated ester of sorbitan and of a saturated, linear or branched fatty acid with a number of moles of ethylene oxide equal to 4; and
   at least one non-silicone fatty substance liquid at a temperature of 25° C. chosen from fatty esters and/or plant oils, wherein the liquid fatty substance is present in an amount ranging from 0.05% to 4% by weight relative to the total weight of the composition,
   wherein the saturated, linear or branched fatty acid comprises from 8 to 18 carbon atoms;
   wherein the at least one cationic surfactant is chosen from quaternary ammonium salts of formula (V)

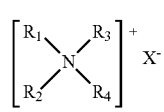

in which $R_1$ to $R_4$, which may be identical or different, are chosen from linear or branched aliphatic radicals having from 1 to 30 carbon atoms and aromatic radicals; and $X^-$ is an anion chosen from halides, phosphates, acetates, lactates, $(C_2-C_6)$alkyl sulfates, alkylsulfonates and alkylarylsulfonates.

2. The composition according to claim 1, wherein the at least one cationic surfactant is chosen from behenyltrimethylammonium chloride, cetyltrimethylammonium chloride, behenylamidopropyl-2,3-dihydroxypropyldimethylammonium chloride, palmitylamido-propyltrimethylammonium chloride, and stearamidopropyldimethylamine.

3. The composition according to claim 1, wherein the at least one cationic surfactant is present in an amount ranging from 0.01% to 10% by weight relative to the total weight of the composition.

4. The composition according to claim 3, wherein the at least one cationic surfactant is present in an amount ranging from 0.05% to 4% by weight relative to the total weight of the composition.

5. The composition according to claim 1, wherein the saturated, linear or branched fatty acid is chosen from lauric acid and stearic acid.

6. The composition according to claim 5, wherein the fatty acid is lauric acid.

7. The composition according to claim 1, wherein the oxyethylenated sorbitan esters are chosen from the monoesters of the saturated, linear or branched fatty acid and of oxyethylenated sorbitan.

8. The composition according to claim 1, wherein the oxyethylenated sorbitan esters are chosen from sorbitan monolaurate oxyethylenated with 4 mol of ethylene oxide (4 EP) and sorbitan monostearate oxyethylenated with 4 mol of ethylene oxide (4 EP).

9. The composition according to claim 1, wherein the oxyethylenated sorbitan ester is sorbitan monolaurate oxyethylenated with 4 mol of ethylene oxide (4 EO).

10. The composition according to claim 1, wherein the oxyethylenated sorbitan ester is present in the composition in an amount ranging from 0.1% to 10% by weight relative to the total weight of the composition.

11. The composition according to claim 10, wherein the oxyethylenated sorbitan ester is present in the composition in an amount ranging from 0.5% to 8% by weight relative to the total weight of the composition.

12. The composition according to claim 1, wherein the liquid fatty esters are chosen from purcellin oil (stearyl 2-ethylhexanoate), isopropyl myristate, isopropyl palmitate, butyl stearate, hexyl laurate, diisopropyl adipate, isononyl isononanoate, 2-ethylhexyl palmitate, 2-octyldodecyl lactate, isostearyl neopentanoate, tridecyl neopentanoate, isocetyl neopentanoate and isoarachidyl neopentanoate, and mixtures thereof.

13. The composition according to claim 1, wherein the plant oils are chosen from sweet almond oil, avocado oil, castor oil, olive oil, joboba oil, sunflower oil, wheat germ oil, sesame oil, groundnut oil, grapeseed oil, soybean oil, rapeseed oil, safflower oil, coconut oil, corn oil, hazelnut oil, shea butter oil, palm oil, apricot kernel oil, liquid jojoba wax, cade oil and beauty-leaf oil, and mixtures thereof.

14. The composition according to claim 1, wherein the liquid fatty substance is present in an amount ranging from 0.5% to 3% by weight relative to the total weight of the composition.

15. The composition according to claim 1, further comprising at least one additional conditioning agent.

16. The composition according to claim 15, wherein the additional conditioning agent is chosen from silicones, cationic polymers, solid carboxylic fatty esters and mixtures thereof.

17. The composition according to claim 1, wherein the cosmetically acceptable aqueous medium comprises water or a mixture of water and of a cosmetically acceptable solvent.

18. The composition according to claim 17, wherein the cosmetically acceptable solvent is chosen from $C_1$-$C_4$ lower alcohols; alkylene glycols; polyol ethers; $C_5$-$C_{10}$ alkanes, and mixtures thereof.

19. The composition according to claim 1, further comprising at least one additive chosen from anionic, nonionic or amphoteric polymers, thickeners, opacifiers, nacreous agents, vitamins, provitamins, fragrances, dyes, organic or mineral particles, preserving agents and pH stabilizers.

20. The composition according to claim 1, wherein the composition is in the form of a hair conditioner, a composition for permanent-waving, relaxing, dyeing or bleaching the hair, or a rinse-out composition to be applied between the two steps of a permanent-waving or hair-relaxing operation.

21. The composition according to claim 1, wherein the composition is a rinse-out hair conditioner.

22. A cosmetic process for treating keratin materials, comprising:
applying to the keratin materials an effective amount of a cosmetic composition;
wherein the cosmetic composition comprises, in a cosmetically acceptable aqueous medium,
at least one cationic surfactant,
at least one oxyethylenated ester of sorbitan and of a saturated, linear or branched fatty acid with a number of moles of ethylene oxide equal to 4, and
at least one non-silicone fatty substance liquid at a temperature of 25° C. chosen from fatty esters and/or plant oils, wherein the liquid fatty substance is present in an amount ranging from 0.05% to 4% by weight relative to the total weight of the composition;
and optionally rinsing off the cosmetic composition,
wherein the saturated, linear or branched fatty acid comprises from 8 to 18 carbon atoms;
wherein the at least one cationic surfactant is chosen from quaternary ammonium salts of formula (V)

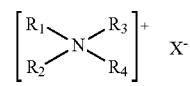

(V)

in which $R_1$ to $R_4$, which may be identical or different, are chosen from linear or branched aliphatic radicals having from 1 to 30 carbon atoms and aromatic radicals; and $X^-$ is an anion chosen from halides, phosphates, acetates, lactates, ($C_2$-$C_6$)alkyl sulfates, alkylsulfonates and alkylarylsulfonates.

* * * * *